(12) United States Patent
Takahara et al.

(10) Patent No.: US 9,810,649 B2
(45) Date of Patent: Nov. 7, 2017

(54) X-RAY FLUORESCENCE ANALYZER

(71) Applicant: HITACHI HIGH-TECH SCIENCE CORPORATION, Minato-ku, Tokyo (JP)

(72) Inventors: Toshiyuki Takahara, Tokyo (JP); Hiroyuki Noda, Tokyo (JP); Ai Masuda, Tokyo (JP)

(73) Assignee: Hitachi High-Tech Science Corporation (JP)

( * ) Notice: Subject to any disclaimer, the term of this patent is extended or adjusted under 35 U.S.C. 154(b) by 75 days.

(21) Appl. No.: 14/956,370

(22) Filed: Dec. 1, 2015

(65) Prior Publication Data

US 2016/0161428 A1   Jun. 9, 2016

(30) Foreign Application Priority Data

Dec. 4, 2014   (JP) ................. 2014-245524

(51) Int. Cl.
  *G01N 23/22*    (2006.01)
  *G01N 23/207*   (2006.01)
  *G01N 23/223*   (2006.01)
  *G21F 3/00*     (2006.01)

(52) U.S. Cl.
  CPC ............. *G01N 23/223* (2013.01); *G21F 3/00* (2013.01); *G01N 2223/076* (2013.01); *G01N 2223/30* (2013.01); *G01N 2223/6113* (2013.01)

(58) Field of Classification Search
  CPC ...... G01N 23/223; G01N 21/64; G01N 21/51; G01N 2223/639; G01N 2223/64; G01N 23/2202; G01N 23/2204; G01N 23/20025; G01N 2223/309; A61B 6/107; A61B 6/485
  USPC .......... 378/20, 208, 209, 44, 57, 68, 69, 195
  See application file for complete search history.

(56) References Cited

U.S. PATENT DOCUMENTS

| | | | | |
|---|---|---|---|---|
| 4,860,329 A | * | 8/1989 | Weiser ................... | G01B 15/02 378/148 |
| 5,309,495 A | * | 5/1994 | Fischer .................. | G01B 15/02 378/206 |

OTHER PUBLICATIONS

"The High Performance FT9500 Series System", Jan. 15, 2014, XP055261311, Retrieved from the Internet on Mar. 29, 2013, URL: http://analityk.com/download/broszury_29.01.20/HHTEUFT9500.pdf, 2 pages.

(Continued)

*Primary Examiner* — Don Wong
(74) *Attorney, Agent, or Firm* — Brinks Gilson & Lione

(57) ABSTRACT

An X-ray fluorescence analyzer includes: a sample stage having a mounting surface on which a sample on which a sample is mounted is mounted; an X-ray source configured to irradiate the sample with primary X-rays and disposed immediately above an irradiation position of the sample; a detector configured to detect fluorescent X-rays emitted from the sample irradiated with the primary X-rays; and a shielding container configured to accommodate the sample stage, the X-ray source, and the detector and includes: a sample chamber configured to accommodate the sample stage; and a door provided at a top of the sample chamber and configured to open and close at least a front half of the sample chamber, wherein the X-ray source and the detector are disposed at a rear half of the sample chamber.

8 Claims, 2 Drawing Sheets

(56) References Cited

OTHER PUBLICATIONS

"Spectro Midex Micro X-Ray Fluorescence Spectrometer for Elemental Analysis: Small Spot, Line Scan and Mapping", 2009, XP055261304, Retrieved from the Internet on Mar. 29, 2016, URL: http://www.spectro.com/~/media/ametekspectro/documents/brochure/spectro_midex_en.pdf, 6 pages.

"Fischerscope X-Ray Product Line XDL", Jul. 2005, XP055261310, Retrieved from the Internet on Mar. 29, 2016, URL: http://www.kks.com.au/wp-content/uploads/2014/01/Helmut-Fischer-Fischerscope-xrf-x-ray-XDL-952-021-x-ray.pdf, 10 pages.

Extended European Search Report in corresponding European Application No. 15197838.4, dated Apr. 6, 2016, 7 pages.

"Fischerscope X-RAY Fluorescence Measuring Systems (XRF)", Fischer Technology, Inc., [searched on Nov. 11, 2015], Internet URL: http://www.fischer-technology.com/en/us/coating-thickness/xrf/.

"Fluorescent X-ray Thickness Meter for Thickness Measurement, FT110 series", Hitachi High-Tech Science Corporation, [searched on Nov. 21, 2014], Internet URL: http://www.hitachi-hightech.com/hhs/product_detail/?pn=ana-ft110.

\* cited by examiner

X-RAY FLUORESCENCE ANALYZER

CROSS-REFERENCE TO RELATED APPLICATION

This application claims priority from Japanese Patent Application No. 2014-245524, filed on Dec. 4, 2014, the entire subject matter of which is incorporated herein by reference.

BACKGROUND

1. Field of the Invention

The present invention relates to an X-ray fluorescence analyzer that can detect toxic substances or the like and that is used for screening products or measuring a film thickness of plating or the like.

2. Description of the Related Art

In a fluorescent X-ray analysis, a spectrum is acquired from energy by irradiating a sample with X-rays emitted from an X-ray source and detecting fluorescent X-rays which are characteristic X-rays emitted from the sample using an X-ray detector, and a qualitative analysis or a quantitative analysis of the sample or film thickness measurement of the sample is performed. Since samples can be rapidly analyzed in a non-destructive manner by the fluorescent X-ray analysis, the fluorescent X-ray analysis is widely used in the fields of process control, quality control, and the like. In recent years, high precision and high sensitivity of the fluorescent X-ray analysis have been achieved, and thus microdetermination is enabled. In particular, the fluorescent X-ray analysis is expected to be a widespread as an analysis method of detecting toxic substances contained in materials, composite electronic parts, or the like.

In general, in an X-ray fluorescence analyzer, an analysis is performed by mounting a sample on a sample stage installed in a sample chamber in an enclosure which is a shielding container and irradiating the sample with primary X-rays from an X-ray source. In the related art, the X-ray fluorescence analyzer has a structure in which a sample is loaded and unloaded by opening and shutting a door installed on the front surface of the enclosure.

Examples of this type of conventional X-ray fluorescence analyzer are disclosed in the following documents.

Non-patent document 1: "Fischerscope X-RAY Fluorescence Measuring Systems (XRF)", Fischer Technology, Inc., [searched on Nov. 11, 2015], Internet URL:
http://www.fischer-technology.com/en/us/coating-thickness/xrf/

Non-patent document 2: "Fluorescent X-ray Thickness Meter for Thickness Measurement, FT110 series," Hitachi High-Tech Science Corporation, [searched on Nov. 21, 2014], Internet URL:
http://www.hitachi-hightech.com/hhs/product_detail/?pn=ana-ft110

In the related art, the following problems may remain.

In the X-ray fluorescence analyzer according to the related art, a sample that is mounted on the sample stage is examined and positioned by through a front door provided on the enclosure by opening the front door. However, there may be some difficulty in viewing the entire sample since the sample is viewed obliquely from above through the front door of the enclosure. If a size of the front door is enlarged to have a better view of the sample, not only the front door but also the enclosure itself should be enlarged in height direction, which makes the entire size of the apparatus to be larger. The conventional X-ray fluorescence analyzer also had a problem in operability in loading and unloading a sample such as a large sized printed circuit through the front door provided on the enclosure, since the front door is not capable to have a wide opening.

SUMMARY OF THE INVENTION

The present disclosure has been made in view of the above-described circumstances, and one of objects of the present disclosure is to provide an X-ray fluorescence analyzer that is capable to improve a visibility of the sample at a measurement position without enlarging the overall size of the apparatus and to more easily load and unload the sample.

According to an exemplary embodiment of the present disclosure, there is provided an X-ray fluorescence analyzer including: a sample stage having a mounting surface on which a sample on which a sample is mounted is mounted; an X-ray source configured to irradiate the sample with primary X-rays and disposed immediately above an irradiation position of the sample; a detector configured to detect fluorescent X-rays emitted from the sample irradiated with the primary X-rays; and a shielding container configured to accommodate the sample stage, the X-ray source, and the detector and includes: a sample chamber configured to accommodate the sample stage; and a door provided at a top of the sample chamber and configured to open and close at least a front half of the sample chamber, wherein the X-ray source and the detector are disposed at a rear half of the sample chamber.

BRIEF DESCRIPTION OF THE DRAWINGS

The above and other aspects of the present disclosure will become more apparent and more readily appreciated from the following description of illustrative embodiments of the present disclosure taken in conjunction with the attached drawings, in which.

DETAILED DESCRIPTION

Hereinafter, an X-ray fluorescence analyzer according to an embodiment of the invention will be described with reference to FIGS. 1 to 3.

Figure 1:
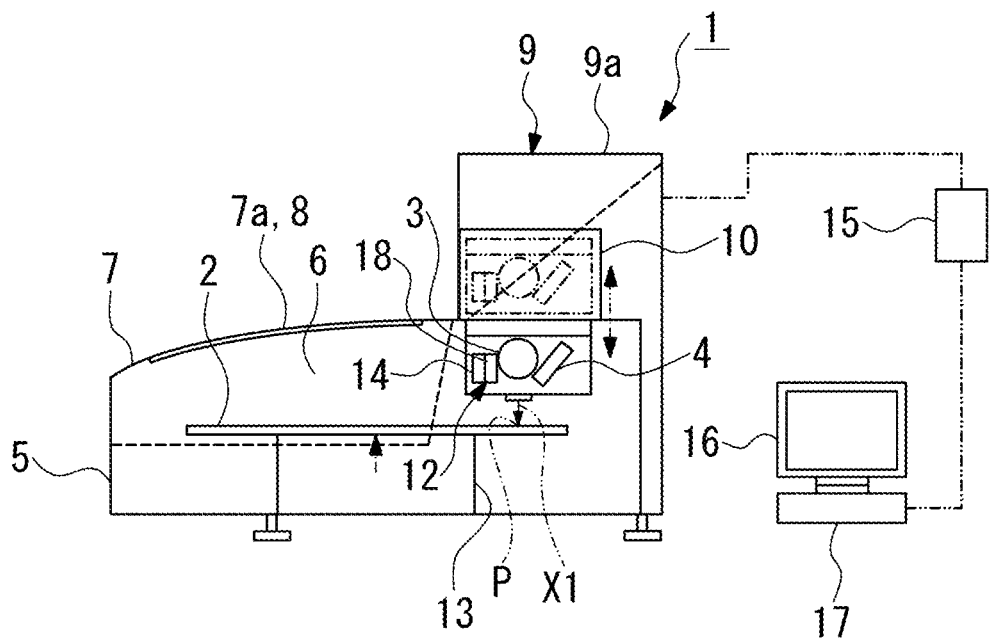
FIG. 1 is a diagram illustrating an internal structure and an entire configuration of an apparatus body in a state in which a door is shut in an X-ray fluorescence analyzer according to an embodiment of the invention.
Figure 2:
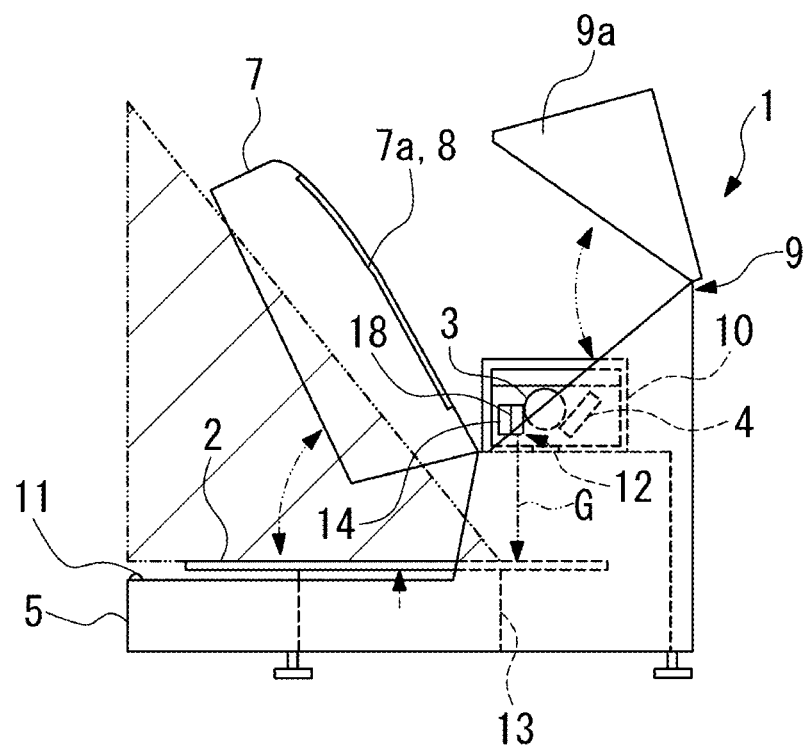
FIG. 2 is a side view illustrating the apparatus body in a state in which the door is opened in the embodiment.
Figure 3:
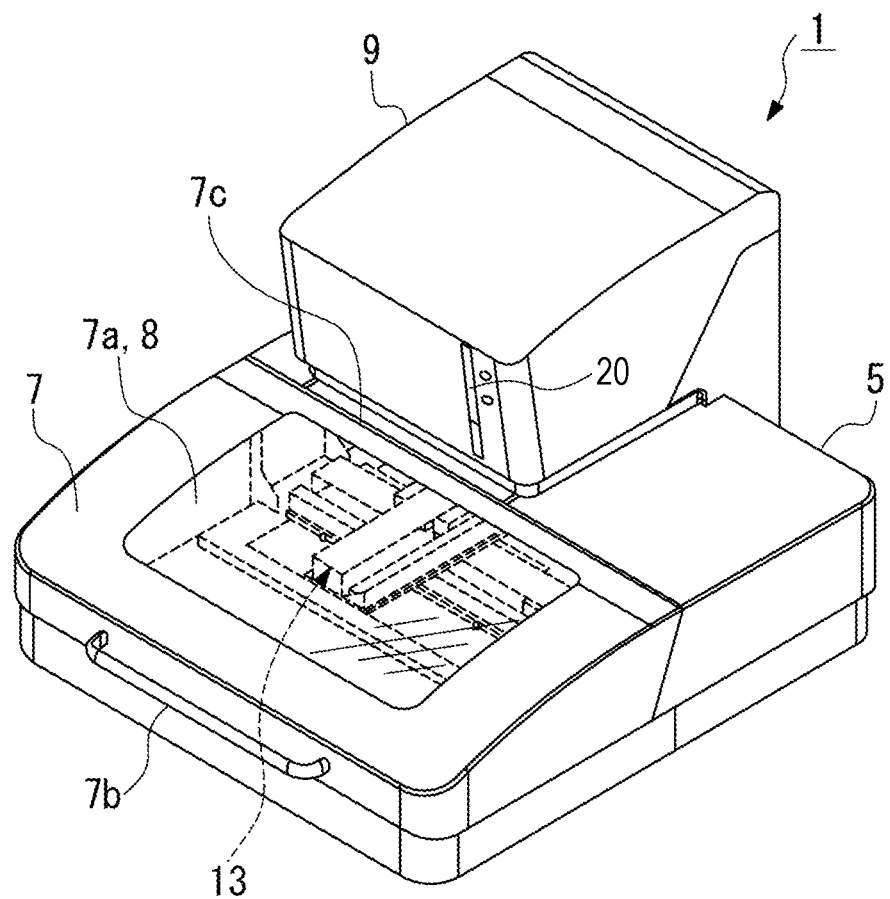
FIG. 3 is a perspective view illustrating the apparatus body of the X-ray fluorescence analyzer according to the embodiment.

As illustrated in FIGS. 1 to 3, an X-ray fluorescence analyzer 1 according to the embodiment is provided with a sample stage 2 having a mounting surface on which a sample can be mounted, an X-ray source 3 disposed immediately above an irradiation position P at which the sample is irradiated with primary X-rays X1 and configured to irradiate the sample with the primary X-rays X1, a detector 4 configured to detect fluorescent X-rays emitted from the sample irradiated with the primary X-rays X1, and a shielding container 5 configured to accommodate at least the sample stage 2, the X-ray source 3, and the detector 4.

The shielding container 5 is an X-ray shielding enclosure and is formed of an iron sheet or the like.

The shielding container 5 is provided with a sample chamber 6 accommodating the sample stage 2 therein and a door 7 opening and shutting at least the first half of the top of the sample chamber 6. When an inner surface size (a length of one side in a plan view) of the sample chamber 6 is defined as "L", the door 7 is formed to be opened up to a position separated by "L×(½)" to "L×(⅔)" from the front end of the shielding container 5.

The X-ray source 3 and the detector 4 are disposed in the back of the door 7.

The irradiation position P with primary X-rays X1 is set to at a position shifted from the center of the sample stage 2. In the embodiment, the irradiation position P is set to a position separated backward by "L×(⅙)" to "L×(⅓)" from the center position of the sample stage 2. In the embodiment, a guide light irradiation mechanism 18 for matching a measurement position is installed above the sample stage 2 and thus the measurement position can be visually checked by irradiating the measurement position (irradiation position P) a visible laser beam as guide light G to illuminate the measurement position.

When the sample measurement position is matched with the irradiation position P (analysis position) with primary X-rays X1 by applying the guide light an image captured by an imaging unit 14 (imaging device) is closely matched visually with the sample measurement position and it is thus easy to check the position matching, thereby improving operability.

A window 7a covered with a transparent plate 8 is formed in the door 7. The transparent plate 8 is formed of, for example, a resin and contains a material such as lead having a high X-ray shielding effect.

The window 7a is formed so large that a rim remains to maintain the strength of the door 7 and enables visually checking the measurement position irradiated with the guide light G from the outside in a state in which the door 7 is shut.

A part of the door 7 in contact with a side surface of a back part of the shielding container 5 is formed in an oblique shape to decrease the weight thereof.

The X-ray fluorescence analyzer 1 is provided with a hood section 9 installed on the shielding container 5 and in the back of the door 7 and connected to the shielding container 5, a vertical moving mechanism 10 that can move the X-ray source 3 and the detector 4 from the shielding container 5 to the hood section 9, a door detecting mechanism 11 configured to detect the opening and shutting of the door 7, a sample detecting mechanism 12 configured to detect a sample mounted on the sample stage 2, a sample stage moving mechanism 13 configured to move the sample stage 2, and the imaging unit 14 configured to capture an image of the sample on the sample stage 2.

The X-ray fluorescence analyzer 1 is also provided with an analyzer 15 connected to the detector 4 and configured to analyze a signal from the detector 4 and a control unit 17 connected to the X-ray source 3, the detector 4, the sample stage moving mechanism 13, the door detecting mechanism 11, the sample detecting mechanism 12, the imaging unit 14, the display unit 16, the analyzer 15, and the like and configured to control these elements.

The shielding container 5, the hood section 9, and the elements accommodating therein are defined as an apparatus body.

The hood section 9 can open and shut at least a part in a state in which the X-ray source 3 and the detector 4 are accommodated therein. That is, a hood opening and shutting portion 9a which can be opened and shut is formed on the hood section 9. As illustrated in FIG. 2, the hood opening and shutting portion 9a has a hinge portion on the back side so as to open widely the front side of the hood section 9.

The hood section 9 is provided with an indicator 20 enabling ON and OFF of irradiation with the primary X-rays X1 from the X-ray source 3. The indicator 20 is formed in a vertically-long band shape on the front surface of the hood opening and shutting portion 9a, and is set to display red when the primary X-rays X1 are emitted and to be turned off when the primary X-rays X1 are not emitted.

The vertical moving mechanism 10 is configured to move the X-ray source 3 and the detector 4 to the hood section 9 when the door detecting mechanism 11 detects that the door 7 is opened.

The vertical moving mechanism 10 is configured to move the X-ray source 3 and the detector 4 to a predetermined height position in the shielding container 5 when the sample detecting mechanism 12 detects a sample on the sample stage 2 and the door detecting mechanism 11 detects that the door 7 is shut.

When a sample is mounted on the sample stage 2, the sample detecting mechanism 12 detects that the sample is on the sample stage 2 by irradiating the sample with the guide light G using a guide light irradiation mechanism 18 and detecting the detection state of a light-receiving unit (not illustrated) such as an optical position detecting device (PSD) or a linear image sensor.

The vertical moving mechanism 10 detects the relative position in the height direction of the measurement position of the sample by irradiating the sample with the guide light G and detecting the detection state in the light-receiving unit and moves the X-ray source 3 and the detector 4 to a predetermined height position in the shielding container 5.

For example, the door detecting mechanism 11 may employ a mechanism for detecting whether an edge of the door 7 comes in contact with a lower portion of the shielding container 5 using a switch.

The door 7 is provided with a hinge portion 7c at the back end thereof so as to be openable from the front surface side and a handle 7b is formed on the front surface of the door 7. A recessed portion instead of the handle 7b may be formed on the front surface of the door 7.

The sample stage moving mechanism 13 is provided with an X stage (not illustrated) configured to move the sample stage 2 in an X direction which is one direction parallel to the mounting surface, a Y stage (not illustrated) configured to move the sample stage 2 in a Y direction parallel to the mounting surface and perpendicular to the X direction, and a θ stage (not illustrated) configured to have a rotation center at the center of the mounting surface and to rotate the sample stage 2 around a rotation axis perpendicular to the mounting surface. These stages are respectively driven by an actuator such as s motor.

The vertical moving mechanism 10 is configured by a motor or the like that moves a unit to which the X-ray source 3, the detector 4, the imaging unit 14, and the guide light irradiation mechanism 18 are attached in a Z direction (vertical direction) perpendicular to the X direction and the Y direction.

The imaging unit 14 is an observation camera on which a CCD or the like is mounted and is installed at a position close to the door 7 above the sample stage 2 so as to image the sample on the sample stage 2.

The X-ray source 3 is an X-ray tube capable of emitting primary X-rays X1 and serves to emit X-rays, which are generated by accelerating thermoelectrons generated from a filament (cathode) in the tube by a voltage applied between the filament (cathode) and a target (anode) and causing the thermoelectrons to collide with W (tungsten), Mo (molybdenum), Cr (chromium), or the like as the target, as the primary X-rays X1 from a window formed of a beryllium foil or the like.

The detector 4 is provided with a semiconductor detection device (for example, a Si (silicon) device which is a pin-structure diode) (not illustrated) and serves to generate a current pulse corresponding to one X-ray photon when the one X-ray photon is incident. The instantaneous current value of the current pulse is in proportion to energy of incident characteristic X-rays. The detector 4 is set to convert the current pulse generated from the semiconductor detection device into a voltage pulse, to amplify the voltage pulse, and to output the voltage pulse as a signal.

The analyzer 15 is a pulse height analyzer (multi-channel analyzer) that acquires a height of a voltage pulse from the signal and generates an energy spectrum.

The control unit 17 is a computer including a CPU and the like and has a function of displaying an image captured by the imaging unit 14 or an analysis result on the display unit 16.

A fluorescent X-ray analyzing method using the X-ray fluorescence analyzer 1 according to the embodiment will be described below.

First, the door 7 is opened to open the top of the front part of the sample chamber 6. At this time, the door detecting mechanism 11 detects that the door 7 is opened and the vertical moving mechanism 10 raises and moves backward the X-ray source 3 and the detector 4 into the hood section 9 based on the detection result. In this state, a sample is mounted on the sample stage 2 along the guide light G emitted from the guide light irradiation mechanism 18.

When the door 7 is shut after the sample is mounted, the door detecting mechanism 11 detects that the door 7 is shut, and the sample detecting mechanism 12 detects the sample on the sample stage 2, the vertical moving mechanism 10 moves down the X-ray source 3 and the detector 4 in the hood section 9 to a predetermined height position in the sample chamber 6 based on the detection results. Thereafter, micro-positioning is performed and the fluorescent X-ray analysis is performed by irradiating the sample with primary X-rays X1 from the X-ray source 3. When the primary X-rays X1 are emitted, the indicator 20 indicates red light.

As described above, in the X-ray fluorescence analyzer 1 according to the embodiment, since the door 7 opening and shutting at least the first half of the top of the sample chamber 6 is provided and the X-ray source 3 and the detector 4 are disposed in the back of the door 7, a large opening is obtained by the door 7 above the front part of the sample chamber 6, the visibility of the sample on the sample stage 2 is improved, and the matching of the measurement position of the sample is facilitated. That is, by disposing the X-ray source 3 and the detector 4 in the back part of the sample chamber 6 (backward from the center of the sample stage 2) and forming the door 7 above the front part of the empty sample chamber 6, the top of the front part of the sample stage 2 can be opened widely and a position observation area (the hatched area in FIG. 2) of the sample on the sample stage 2 is enlarged.

The hood section may be horizontally asymmetric as well as asymmetric in the front-back direction as illustrated in FIG. 3. That is, the hood section may be disposed on the left side or the right side of the center (the center in the horizontal direction) of the sample chamber in a front view thereof, and thus the shielding container and the hood section may be horizontally asymmetric.

As a result, the X-ray source 3 and the detector 4 are also moved. Since the hood section is horizontally asymmetric, an empty space is formed in the back part of the shielding container 5 (on the back side of the door 7) and the display unit or the like may be disposed in the empty space, for example, thereby reducing an installation space of an X-ray fluorescence analyzer for measuring a large printed circuit board.

Since the top of the front part of the sample chamber 6 is opened widely by opening the door 7, a sample such as a large printed circuit board can be easily loaded and unloaded without sacrificing the operability. Since the top of the front part of the sample chamber 6 can be opened and shut by the door 7, a process of detaching a large case body (shielding container) or the like in the related art is not necessary at the time of maintenance.

Since the window 7a covered with the transparent plate 8 is formed in the door 7, the measurement position of the sample mounted on the sample stage 2 can be visually checked through the window 7a.

It is possible to finely adjust the measurement position of the sample by applying guide light G in a state in which the door 7 is shut and moving the sample stage 2.

When the door 7 is shut, the shielding container 5 is air-tightly sealed, an effect of preventing or suppressing exposure in the analysis in which the X-ray source 3 is turned on is improved, and it is thus possible to safely analyze fluorescent X-rays.

Since the hood section 9 disposed on the shielding container 5 and in the back of the door 7 and connected to the shielding container 5 and the vertical moving mechanism 10 vertically moving the X-ray source 3 and the detector 4 and moving the X-ray source 3 and the detector 4 from the shielding container 5 to the hood section 9 are provided, the X-ray source 3 and the detector 4 can be moved back into the hood section 9 by the vertical moving mechanism 10 in loading and unloading a sample to and from the sample chamber 6 and it is thus possible to improve the operability and to facilitate loading and unloading of the sample.

Since at least a part of the hood section 9 can be opened and shut in a state in which the X-ray source 3 and the detector 4 are accommodated therein, it is possible to improve the operability of detachment, attachment, and maintenance of the X-ray source 3 and the detector 4 by opening the hood section 9.

When the door detecting mechanism 11 detects that the door 7 is opened, the vertical moving mechanism 10 moves the X-ray source 3 and the detector 4 to the hood section 9. Accordingly, since the X-ray source 3 and the detector 4 are automatically moved backward to the hood section 9 by opening the door 7, it is possible to prevent the backward movement from being forgotten in mounting a sample.

When the sample detecting mechanism 12 detects the sample on the sample stage 2 and the door detecting mechanism 11 detects that the door 7 is shut, the vertical moving mechanism 10 moves the X-ray source 3 and the detector 4 to a predetermined height position in the shielding container 5. Accordingly, by shutting the door 7 after a sample is mounted on the sample stage 2, the X-ray source 3 and the detector 4 are automatically moved down and can be coarsely positioned in the height direction. As a result, fine positioning only has to be performed at the time of measurement and movement of a long stroke can be saved, thereby achieving high convenience and shortening the time.

Since the hood section 9 is provided with the indicator 20 visually indicating ON and OFF of irradiation with primary X-rays X1 from the X-ray source 3, it is possible to clearly monitor the operating situation of the apparatus.

Since the door 7 includes the hinge portion 7c at the back end thereof so as to be opened from the front surface side and the handle 7b is formed on the front surface of the door 7, it is possible to easily open and shut the door 7 by hooking a finger on the handle 7b and moving up and down the edge of the door 7.

As described with reference to the embodiment, in the X-ray fluorescence analyzer according to the present disclosure, since a door that enables to open and close of at least the first half of the top of the sample chamber is provided, and the X-ray source and the detector are disposed in the back of the door, a large opening may be obtained by the door above the front part of the sample chamber. Accordingly, it is possible to improve visibility of the sample on the sample stage.

Therefore, it is possible to facilitate matching of the measurement position of the sample, to easily load and unload a sample such as a large printed circuit board without sacrificing operability, and to save an installation space in comparison with the same level X-ray fluorescence analyzer for a large sample.

The present disclosure is not limited to the specific example as described in the above with respect to the embodiment, and the X-ray fluorescence analyze may be modified in various forms without departing from the spirit and scope of the present disclosure.

For example, in the above-described embodiment, an energy-dispersion type X-ray fluorescence analyzer is described, which measures energy and intensity of X-rays using a pulse height analyzer. However, a wavelength-dispersion type X-ray fluorescence analyzer may also be employed, which disperses fluorescent X-rays using a dispersive crystal and measures a wavelength and intensity of the X-rays.

When the door 7 is opened and a sample is loaded or unloaded, the backward movement of the X-ray source 3 and the detector 4 or the coarse position adjustment before the door 7 is shut and the fluorescent X-ray analysis is started may be performed manually.

What is claimed is:

1. An X-ray fluorescence analyzer comprising:
   a sample stage having a mounting surface on which a sample is mounted;
   an X-ray source configured to irradiate the sample with primary X-rays and disposed immediately above an irradiation position of the sample;
   a detector configured to detect fluorescent X-rays emitted from the sample irradiated with the primary X-rays;
   a shielding container configured to accommodate the sample stage, the X-ray source, and the detector and includes:
   a sample chamber configured to accommodate the sample stage;
   a door provided at a top of the sample chamber and configured to open and close at least a front half of the sample chamber,
   wherein the X-ray source and the detector are disposed at a rear half of the sample chamber;
   a hood section disposed on the shielding container at the rear half thereof and connected to the shielding container; and
   a vertical moving mechanism configured to vertically move the X-ray source and the detector and move the X-ray source and the detector between a first position inside the shielding container and a second position inside the hood section.

2. The X-ray fluorescence analyzer according to claim 1, wherein the door is provided with a window covered with a transparent plate.

3. The X-ray fluorescence analyzer according to claim 1, wherein the hood section is disposed at a position shifted to the left side or the right side from the center of the sample chamber when viewed from the front side, and wherein the shielding container and the hood section are disposed to be horizontally asymmetric.

4. The X-ray fluorescence analyzer according to claim 1, wherein at least a part of the hood section is configured to be opened and shut in a state where the X-ray source and the detector are accommodated therein.

5. The X-ray fluorescence analyzer according to claim 1 further comprising:
   a door detecting mechanism configured to detect opening and shutting of the door,
   wherein the vertical moving mechanism is configured to move the X-ray source and the detector at the second position when the door detecting mechanism detects that the door is opened.

6. The X-ray fluorescence analyzer according to claim 5 further comprising:
   sample detecting mechanism configured to detect that the sample is mounted on the sample stage,
   wherein the vertical moving mechanism is configured to move the X-ray source and the detector to a predetermined height position in the shielding container when the sample detecting mechanism detects the sample on the sample stage and the door detecting mechanism detects that the door is shut.

7. The X-ray fluorescence analyzer according to claim 1, wherein the hood section is provided with an indicator indicating ON and OFF of irradiation with primary X-rays from the X-ray source.

8. The X-ray fluorescence analyzer according to claim 1, wherein the door is provided with a hinge portion at a rear side and configured to be openable from a front side, and
   wherein the door is provided with a handle or a recessed portion at the front side.

* * * * *